United States Patent
Steer

[11] Patent Number: 6,129,716
[45] Date of Patent: Oct. 10, 2000

[54] OSTOMY BAG CONTAINING MICROENCAPSULATED MALODOR COUNTERACTANT MATERIAL

[75] Inventor: Graham E. Steer, London, United Kingdom

[73] Assignee: Bristol-Myers Squibb Company, New York, N.Y.

[21] Appl. No.: 09/038,439

[22] Filed: Mar. 11, 1998

[30] Foreign Application Priority Data

Mar. 17, 1997 [GB] United Kingdom .................... 9705492

[51] Int. Cl.[7] ....................................... A61F 5/44
[52] U.S. Cl. .......................... 604/333; 604/332; 604/339; 604/338
[58] Field of Search ................... 604/333, 332, 604/339, 338

[56] References Cited

U.S. PATENT DOCUMENTS

| 3,490,454 | 1/1970 | Golfarb et al. ......................... 604/359 |
| 3,804,091 | 4/1974 | Nolan et al. ........................... 604/333 |
| 4,372,308 | 2/1983 | Steer et al. ............................. 604/333 |
| 5,116,139 | 5/1992 | Young et al. ........................... 604/333 |
| 5,411,496 | 5/1995 | Homa ..................................... 604/333 |

FOREIGN PATENT DOCUMENTS 2 268 882  1/1994  United Kingdom .

*Primary Examiner*—John G. Weiss
*Assistant Examiner*—Miley Craig Peppers, III
*Attorney, Agent, or Firm*—Stuart E. Krieger

[57] ABSTRACT

A container for odorous material (in the present case an ostomy bag), consists of a front wall (10) and a rear wall (12) welded together around a peripheral seam (14). The walls are made of a plastics material through which odorous gas can permeate. The container carries or contains malodor counteractant material to counter, or mask, the odor. The malodor counteractant material may be provided in microencapsulated form, and coated (at 28) on the interior faces of the walls, or carried on an article (54) placed within the container.

4 Claims, 3 Drawing Sheets

OSTOMY BAG CONTAINING MICROENCAPSULATED MALODOR COUNTERACTANT MATERIAL

BACKGROUND OF THE INVENTION

This invention relates generally to improvements relating to hygiene and medical products. The invention is particularly suitable for personal hygiene projects such as ostomy bags, but the invention is not limited exclusively to such use.

The conventional approach to the manufacture of ostomy bags has been to use a material which is impermeable to gas, in order to prevent unpleasant odours from leaking by seepage of gas through the bag wall. Such odours are present in flatus, and are also produced by bacterial action in decomposing faecal matter. The human nose is extremely sensitive to such odours (usually caused by hydrogen sulphide gas), and it is critical for customer acceptance that no unpleasant odours be allowed to escape while the bag is worn. Typically, a vent with a filter is provided through which filtered gas can escape to avoid the build up of gas within the bag. However, the effect of the filter will be wasted if even small amounts of odour-carrying gas are permitted to seep through the bag walls.

In order to achieve the necessary gas-impermeability, a gas-impermeable barrier layer is usually included in the plastics laminate constituting the bag wall material. The most common, and effective, barrier material is polyvinylidene chloride (PVDC). However, PVDC is expensive, and is a difficult material to handle. There are growing safety and environmental concerns regarding the safe disposal of PVDC, particularly by incineration. Moreover, PVDC has a highly crystalline structure, which makes the laminate "noisy" in the sense that the material will crackle or rustle when it moves, or is bent, or slides under a person's clothing. Such noises can be embarrassing for the wearer of the bag.

The present invention has been devised bearing such problems in mind.

In a first aspect, the invention provides a container for carrying or collecting odorous material, wherein the container carries or contains microencapsulated malodour counteractant material.

In a closely-related second aspect, the invention provides an ostomy bag carrying or containing microencapsulated malodour counteractant material.

The invention can alleviate the need to provide a gas-impermeable barrier layer (e.g. of PVDC) in the wall material of the container. Instead, wall material can be used which does allow permeation of gas through the wall. The malodour counteractant is released and is able to counter the unpleasant odour within the bag. Therefore, any gas which does permeate through the container wall will not have an unpleasant odour.

Microencapsulation is a known technique in which a very small quantity of a material is encapsulated within a layer, or skin of encapsulant material. In the present case encapsulation traps the malodour counteractant material, thereby preserving its state and preventing dispersal or substantial decay of its malodour counteractant properties. The encapsulant is such that it is able to release the encapsulated material, for example, by mechanical rupture, temperature dependent release, or moisture-activated release. This can provide controlled, progressive release of the malodour counteractant to provide continued odour suppression.

Microencapsulation has been used in the past to provide so-called "scratch and sniff" smells. Small quantities of a fragrance are encapsulated within an encapsulant material, usually gelatin based, which is then applied to card or paper. When the microencapsulated material is scratched or rubbed, the gelatin skin ruptures, releasing the fragrance.

The microencapsulated malodour counteractant may, for example, be carried on an interior face of a wall of the bag or container. Preferably, the microencapsulated material is carried on the faces of a plurality of walls, more preferably on the interior faces of all of the bag walls.

In the case of a container or bag which has walls welded together along one or more seams, the microencapsulated material may be carried over most of the interior face of the bag wall except the region of the weld. The microencapsulated material might otherwise interfere with the weld around the periphery.

In addition to, or as an alternative to, the microencapsulated material being carried on the wall of the bag or container, the microencapsulated material may be carried on an article placed within the bag or container. For example, the microencapsulated material may be carried on an absorbent or a superabsorbent article, such as that described in GB-A-2,301,350.

In a closely-related aspect, the invention provides a product for insertion in an ostomy bag, the product carrying microencapsulated malodour counteractant material.

In a further closely-related aspect, the invention provides a product comprising super-absorbent material and microencapsulated malodour counteractant material.

In a further closely-related aspect, the invention provides a medical or hygiene product carrying or containing a microencapsulated active material such that, in use, the active material is releasable from the microencapsulated state.

The term "active material" is intended to cover any material providing a medical or hygiene function, in use. For example, such materials include malodour counteractants, medicaments, and disinfectants.

In a closely related aspect, the invention provides a container for containing or collecting unpleasantly odorous material, the container having at least one wall made of material which is at least partly permeable to gas, the container carrying or containing a malodour counteractant material to counter the unpleasant odour of gas leaking through the container wall.

Preferably, the container further comprises a vent providing a main gas escape path for gas.

The term "at least partly permeable" is intended to refer to the material being such that at least some gas can leak through the wall in sufficient quantity to produce a detectable unpleasant odour outside the container, were it not for the presence of the malodour counteractant.

Preferably, the container is an ostomy bag.

In a closely-related further aspect, the invention provides a method of applying a malodour counteractant to a product for ostomy use, the method comprising applying the malodour counteractant in a microencapsulated state.

In a yet further closely related aspect, the invention provides a method of applying an active material to a medical or hygiene product, the method comprising applying the active material in a microencapsulated state.

In the above methods, the microencapsulated material may be solution coated onto the product, or it may be "printed" by any suitable printing technique, such as silk screen printing, tampo-offset printing, or ink-jet printing.

BRIEF DESCRIPTION OF THE DRAWINGS

Embodiments of the invention are now described by way of example only, with reference to the accompanying drawings, in which.

DETAILED DESCRIPTION OF THE DRAWINGS

Figure 2:
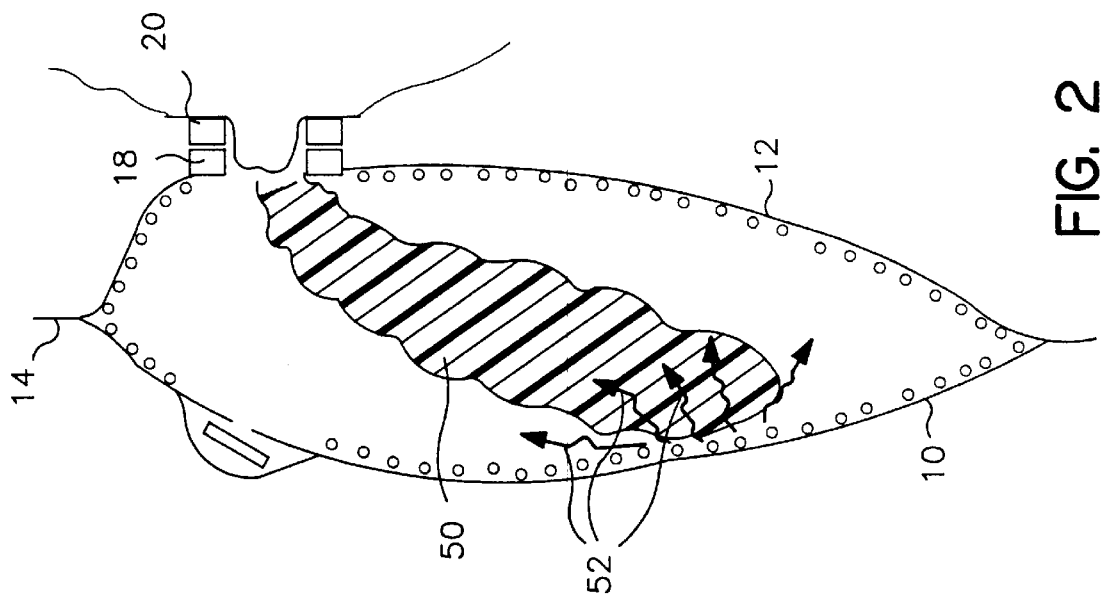
FIG. 2 is a schematic view showing activation of the counteractant material used in FIG. 1.
Figure 1:
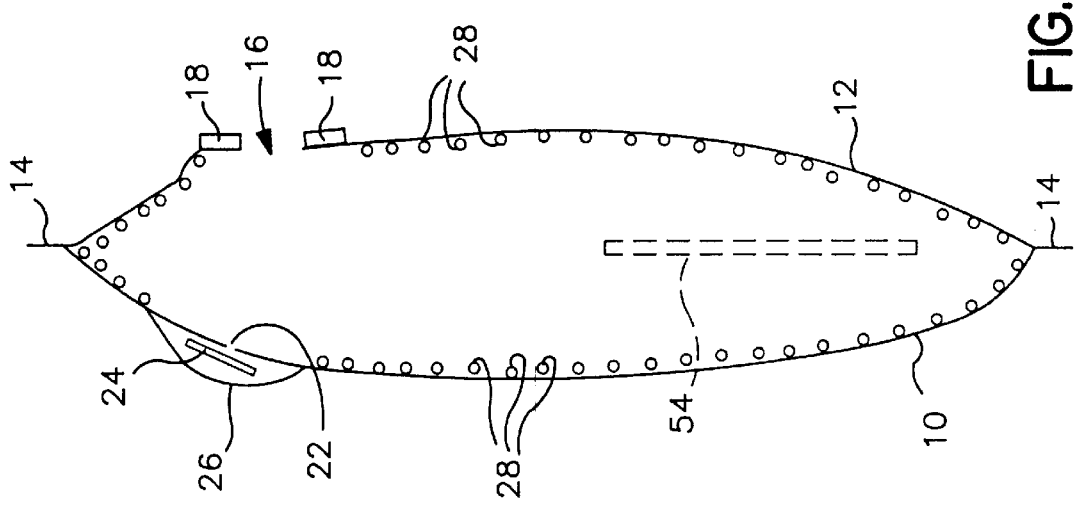
FIG. 1 is a schematic section through an ostomy bag embodying the invention.

Referring to FIGS. 1 and 2, an ostomy bag consists of a front wall 10 and a rear wall 12 welded together around their periphery to form a welded seam 14. In this embodiment, the front and rear walls are made of the same plastics material. In contrast to the prior art, in this embodiment the wall material does not need to be impermeable to gas, and it does not require the presence of a gas-impenetrable barrier layer. The wall may be of any suitable of mono-layer or laminate, plastics film material, such as thermoplastic elastomers, polyetherurythanes and polyolefins.

In an upper region, the rear wall 12 has a stomal orifice 16 which is surrounded by a coupling member 18 on the exterior of the bag. In use, the coupling member 18 enables the bag to be coupled to a body-side coupling member 20 (FIG. 2) worn on the ostomate's peristomal area. Typically, the coupling parts are held together by adhesive or by a mechanical locking arrangement.

In an upper region, the front wall 10 has a vent aperture 22 over which a filter element 24 (for example of activated charcoal) and a perforated cover 26 are sealed. The vent enables excess gas in the bag to escape, to prevent a build up of gas and thereby pressure inside the ostomy bag. Although the bag wall is of a material which is at least partly permeable to gas, the rate of gas transpiration through the wall material will generally not be sufficient to allow all of the gas to escape. Typically, the amount of gas entering the bag through the stomal orifice can be as much as 100 milliliters per minute, on an intermittent basis.

In accordance with the principles of one aspect of the invention, the ostomy bag carries or contains a malodour counteractant. The purpose of the malodour counteractant is to absorb the unpleasant odour in the bag, or to modify or mask the odour with a counter-fragrance. Thus, the unpleasantness of the odour in the bag can be reduced, such that any gas leaking through the material of the walls 10 and 12 will not cause unpleasant smells.

Figure 5:
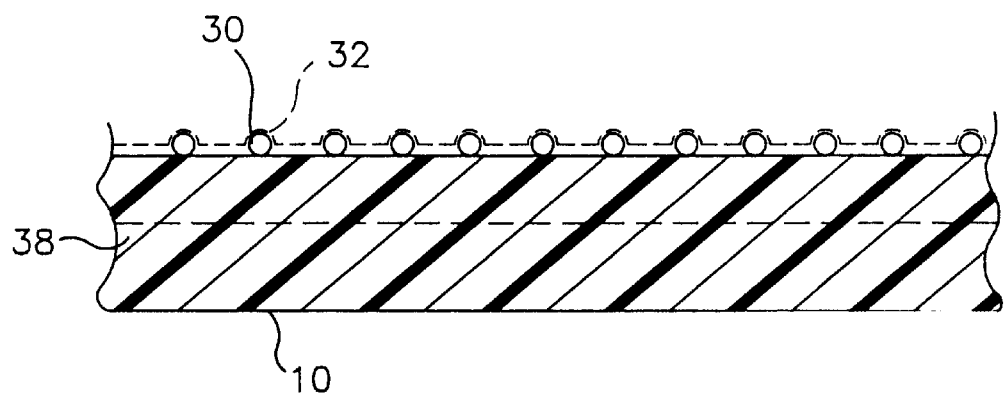
FIG. 5 is an enlarged view showing a detail of FIG. 1.

In the present embodiment, the malodour counteractant is provided in a microencapsulated form (depicted by numeral 28) and is carried on the interior faces of the front and rear walls 10 and 12. Referring to FIG. 5, the counteractant material is encapsulated as micro-spheres or beads 30 which are surrounded by a skin or layer 32 of encapsulant material.

Microencapsulation is a known technique in which very small globules or beads of material, usually of the order of a few microns in size, are surrounded by a coating or skin of encapsulant. The encapsulant traps the material preserving its state and preventing the material from dispersing. The material can be released from the encapsulant at an appropriate time by any suitable method depending on the encapsulant material. For example, release may occur in response to mechanical disturbance or rupture of the encapsulant, or to chemical breakdown, or to contact with moisture (e.g. by dissolving the encapsulant) or to temperature (e.g. by melting of the encapsulant).

The encapsulant may be solid. Alternatively, the encapsulant may be of an interphase material, such as gelatine based material, or gum composites, or a combination tailored to suit the material being encapsulated. The encapsulant may also be tailored to suit the material on which the microencapsulated beads are carried, to adhere to the surface of the carrier material. Referring to FIG. 5, the bag wall material may, if desired, be a monolayer (as shown), or it may be a laminate having a surface layer (shown schematically by broken line 38) to which the encapsulant material will adhere.

The material within the beads may be solid, or it may be fluid, for example, an oil based or water based liquid, or a gas.

One technique for preparing microencapsulated material is to emulsify a fluid material to be encapsulated (e.g. an oil based material) with encapsulant fluid, to produce the microspheres or beads at the liquid phase interface. The suspended microencapsulated material can then be applied to a surface on which it is to be carried, by any suitable application technique. For example, the microencapsulated material may be solution coated directly onto the plastics film, using a suitable solvent (for example, water). After drying, this would leave a thin uniform dispersion of microspheres on the plastics film surface.

Alternatively, the microspheres may be applied to the surface in a uniform or random matrix or array using printing techniques, such as screen printing, tampo-offset printing, or ink-jet printing.

Many techniques are known for creating and applying microencapsulated material. For example, the reader is referred to U.S. Pat. No. 4,303,432 and WO-A80/00439 (Microcel Technology, Inc.).

Figure 3:
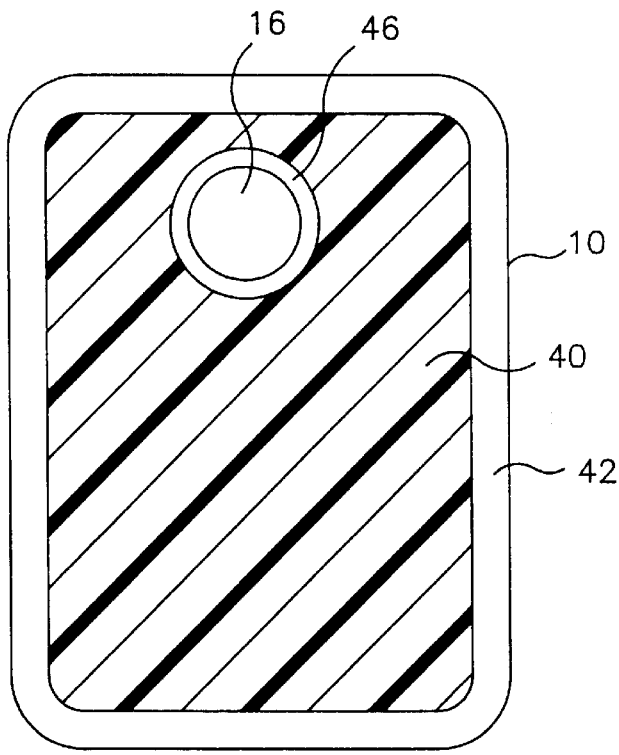
FIGS. 3 and 4 are views showing the areas of application of the malodour counteractant during production of the ostomy bag.
Figure 4:
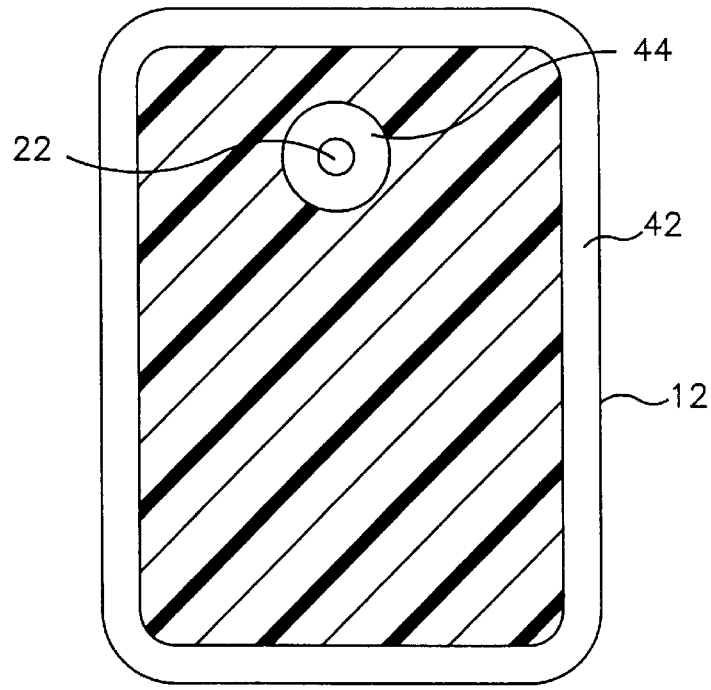

In the present embodiment, the microencapsulated malodour counteractant material is applied over substantially the entire area of the walls 10 and 12, except in predetermined areas required for welding to form the finished ostomy bag. The microencapsulated material is omitted from these areas as it might interfere with the integrity or strength of the welds, and might also cause unwanted release of malodour counteractant during the welding process. In FIGS. 3 and 4, the cross-matched areas 40 represent the area over which the microencapsulant material is applied. In particular, a peripheral region 42 of both the front wall 10 and the rear wall 12 is left clear for welding the seam 14, as are an annular region 44 surrounding the vent aperture 22 to which the cover 26 is welded, and an annular region 46 surrounding the stoma aperture 16 to which the coupling member 18 is welded.

In use, the microencapsulation of the malodour counteractant prevents the counteractant material from dispersing and wasting away prior to use of the ostomy bag. When the bag is worn by an ostomate, and faecal matter (illustrated by numeral 50 in FIG. 2) enters the bag and contacts the bag wall, the microencapsulant can be activated by any suitable release mechanism depending on the material of the microencapsulant (e.g. by temperature, moisture, mechanical rupture) to release the malodour counteractant, as illustrated schematically at 52. The microencapsulation enables the release of malodour counteractant to be controlled in relation to the contact area between the faecal matter and the bag wall. Thus, release of the malodour counteractant can be controlled to some extent by the amount of faecal matter in the bag, and the rate of arrival of faecal matter. In particular, the counteractant material can be released progressively as more faecal matter is collected and contacts more area of the bag wall.

Figure 6:
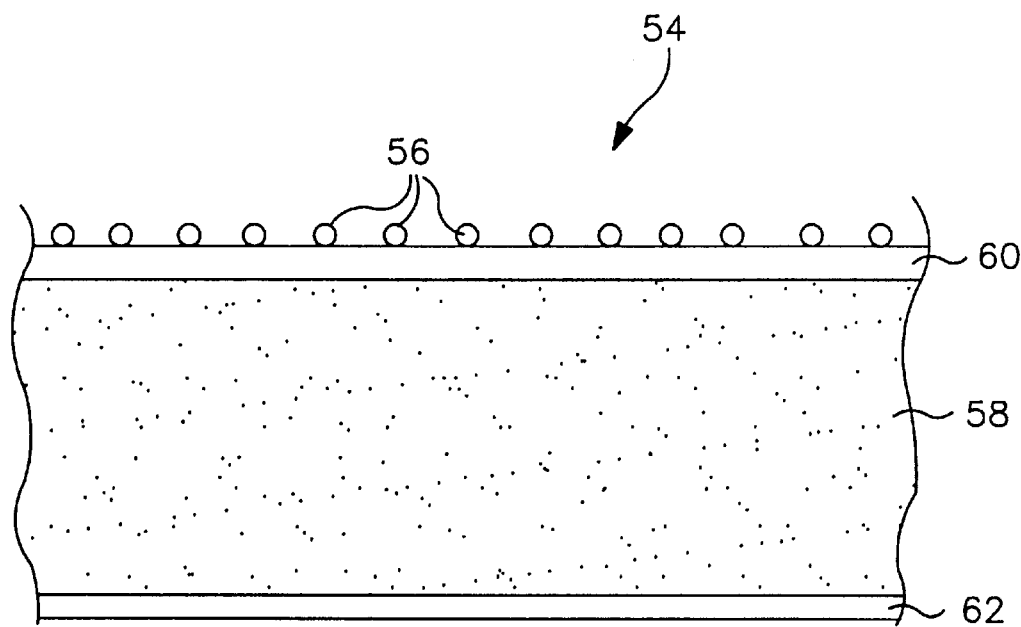
FIG. 6 is a schematic view of an absorbent product carrying microencapsulated malodour counteractant, for insertion in an ostomy bag.

If desired an absorbent article 54 (FIG. 1) may be placed inside the ostomy bag to absorb liquid. For example, the article 54 may include superabsorbent material, such as that described in our UK Patent Application GB-A-2,301,350. Referring to FIG. 6, the article 54 may also carry malodour counteractant, for example, in microencapsulated form, as depicted by spheres 56. In the FIG. 6 embodiment, the absorbent article 54 consists of consolidated superabsorbent powder 58 carried between upper and lower tissues 60 and 62 respectively. The microencapsulated superabsorbent is applied to the upper tissue 60, but it could be applied to either or both tissues as required.

In very general terms, the malodour counteractant may be provided in a non-microencapsulated form, and have the same function of absorbing or masking unpleasant odours which may leak through the wall material of the bag. The malodour counteractant could, for example, be provided in the form of a strip, or tablet, or other article placed inside the bag. However, microencapsulation enables the counteractant material to be provided in a form having a large surface area, and which can achieve controlled release of the malodour counteractant.

Although the above embodiments illustrate the invention in the field of ostomy, it will be appreciated that the invention has broader applications. For example, the invention may be used in any hygiene or medical product in which the controlled release of an active material, such as a malodour counteractant, medicament, or disinfectant, is required.

Although features believed to be of particular importance have been identified in the foregoing description and in the appended claims, the Applicant claims protection for any novel feature or combination of features described herein and/or illustrated in the accompanying drawings.

I claim:

1. An ostomy bag comprising, a pouch having a front wall and rear wall welded together around their peripheries, one of said walls having a stomal orifice for receiving waste from a stoma, and an article within said pouch having microencapsulated malodor counteractant material thereon.

2. The ostomy bag of claim 1, wherein at least one of said pouch walls has a vent for allowing gas to escape and a filter covering said vent for filtering odor passing through said vent.

3. A method for making an ostomy bag comprising the steps of:

forming a pouch having a front wall and rear wall welded together around their peripheries, providing a stomal orifice in one of said walls for receiving waste from a stoma, providing an article in said pouch having an outer surface, the outer surface carrying microencapsulated malodor counteractant material thereon.

4. The method of claim 3 further comprising the step of providing the article with absorbent capability.

* * * * *